US010213413B2

(12) United States Patent
Sizun et al.

(10) Patent No.: US 10,213,413 B2
(45) Date of Patent: Feb. 26, 2019

(54) ANTIVIRAL AGENTS DIRECTED AGAINST RESPIRATORY SYNCYTIAL VIRUS

(71) Applicants: CENTRE NATIONAL DE LA RECHERCHE SCIENTIFIQUE (CNRS), Paris (FR); INSTITUT NATIONAL DE LA RECHERCHE AGRONOMIQUE, Paris (FR); Institut Pasteur, Paris (FR); UNIVERSITÉ PARIS-SUD, Orsay (FR)

(72) Inventors: Christina Sizun, Palaiseau (FR); Stéphane Duquerroy, Saint Ouen (FR); Jean-François Eleouet, Breuillet (FR); Felix Rey, Gif sur Yvette (FR); Anny Slama Schwok, St Aubin (FR); Didier Desmaele, Fresnes (FR); Patrick Couvreur, Villebon sur Yvette (FR); Bogdan Tarus, Moulins les Metz (FR)

(73) Assignees: CENTRE NATIONAL DE LA RECHERCHE SCIENTIFIQUE (CNRS), Paris (FR); INSTITUT NATIONAL DE LA RECHERCHEAGRONOMIQUE, Paris (FR); Institut Pasteur, Paris (FR); UNIVERSITÉ PARIS-SUD, Orsay (FR)

( * ) Notice: Subject to any disclaimer, the term of this patent is extended or adjusted under 35 U.S.C. 154(b) by 0 days.

(21) Appl. No.: 15/523,995

(22) PCT Filed: Nov. 5, 2015

(86) PCT No.: PCT/EP2015/075861
§ 371 (c)(1),
(2) Date: May 3, 2017

(87) PCT Pub. No.: WO2016/071470
PCT Pub. Date: May 12, 2016

(65) Prior Publication Data
US 2017/0360752 A1 Dec. 21, 2017

(30) Foreign Application Priority Data
Nov. 6, 2014 (EP) .................................... 14306774

(51) Int. Cl.
A61K 31/415 (2006.01)
C07D 231/14 (2006.01)
A61K 45/06 (2006.01)
A61K 31/045 (2006.01)
A61K 31/19 (2006.01)
A61K 31/513 (2006.01)
A61K 31/522 (2006.01)
A61K 31/662 (2006.01)
A61K 31/675 (2006.01)
A61K 31/7056 (2006.01)
A61K 31/7072 (2006.01)
A61K 31/7076 (2006.01)
A61K 31/7088 (2006.01)
A61K 31/7105 (2006.01)

(52) U.S. Cl.
CPC .......... *A61K 31/415* (2013.01); *A61K 31/045* (2013.01); *A61K 31/19* (2013.01); *A61K 31/513* (2013.01); *A61K 31/522* (2013.01); *A61K 31/662* (2013.01); *A61K 31/675* (2013.01); *A61K 31/7056* (2013.01); *A61K 31/7072* (2013.01); *A61K 31/7076* (2013.01); *A61K 31/7088* (2013.01); *A61K 31/7105* (2013.01); *A61K 45/06* (2013.01); *C07D 231/14* (2013.01)

(58) Field of Classification Search
None
See application file for complete search history.

(56) References Cited

U.S. PATENT DOCUMENTS 6,506,738 B1   1/2003   Yu et al.
2013/0102607 A1   4/2013   Cass et al.

OTHER PUBLICATIONS

Fierros et al., Regioselective enzyme-catalyzed synthesis of pyrazole-containing podands, Heterocycles, 36(9):2019-34 (1993).
International Search Report and Written Opinion, International Application No. PCT/EP2015/075861, dated Jan. 11, 2016.
Substance Record for SID 168291472 (MCULE-3648967095) (2013).
Tiong-Yip et al., Characterization of a respiratory syncytial virus L protein inhibitor, Antimicrob. Agents Chemother., 58(7):3867-73 (2014).
Woods et al., Inhibition of respiratory synctial virus replication in vitro by a pyrazole dicarboxamide analog of ribavirin, Antiviral Chem Chemother., 5(5):340-3 (1994).

*Primary Examiner* — Kamal A Saeed
(74) *Attorney, Agent, or Firm* — Marshall, Gerstein & Borun LLP

(57) ABSTRACT

The present invention relates to N1-benzyl substituted pyrazoles as antiviral agents directed against respiratory syncytial virus.

9 Claims, No Drawings

ANTIVIRAL AGENTS DIRECTED AGAINST RESPIRATORY SYNCYTIAL VIRUS

FIELD OF THE INVENTION

The present invention relates to new antiviral agents directed against respiratory syncytial virus.

BACKGROUND OF THE INVENTION

Respiratory Syncytial Virus (RSV) is the most important viral agent causing acute lower respiratory infections in infants worldwide. Almost all children have been infected at the age of 3. Since it is a leading cause of hospitalization among infants, RSV represents a high burden on health care systems. It is also a cause of serious lower respiratory infections in immunocompromised and elderly adults.

Currently, there are only two approved drugs for use in patients having or at risk of having an RSV infection, namely ribavirin and palivizumab. No RSV vaccine is presently available for humans, and the complexity of the immune response to RSV infections coupled to the constraints imposed by pediatric applications render the development of an RSV vaccine particularly challenging.

Ribavirin is a nucleoside analog used for therapeutic intervention, especially for treating RSV infections in individuals at high risk for severe disease. However, ribavirin is non-specific to RSV. In addition, there is limited evidence of the actual benefits provided by ribavirin but increasing proofs of toxic and teratogenic properties of such compound. Consequently, the use of ribavirin is inacceptable particularly in infants and children.

Palivizumab is a humanized monoclonal antibody targeting the RSV fusion protein and is currently used for preventive purposes. Monthly prophylaxis with Palivizumab injections reduces RSV hospitalizations by approximatively 50%. However it is extremely expensive, and cost-benefit analyses showed to be mixed. Moreover, the type of administration is generally not acceptable for an infant population. Therefore, its current use is generally limited to high-risk pediatric patients.

There is thus an obvious and urgent need for a new therapeutic strategy for specifically targeting RSV with an improved efficiency.

SUMMARY OF THE INVENTION

In a first aspect, the invention relates to an agent for use for treating an infection by respiratory syncytial virus (RSV),
wherein said agent is represented in formula (I):

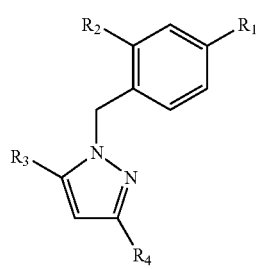

Formula (I)

wherein:
R1 and R2 are identical or different and are independently chosen among hydrogen, hydroxyl, halogen, haloalkyl, alkyl, aryl, arylalkyl, nitro, cyano, amino, alkoxy, alkoxyalkyl, heteroaryl, cycloalkyl and heterocyclyl; and R3 and R4 are identical or different and are independently chosen among carboxylate, ester, substituted or non-substituted alkyloxycarbonyl preferably a substituted or non-substituted C1-C6 alkyloxycarbonyl, halogen, haloalkyl, alkyl, aryl, arylalkyl, nitro, cyano, amino, alkoxy, alkoxyalkyl, heteroaryl, cycloalkyl, heterocyclyl, boronate, phosphate, phosphonate, sulfinyl, sulfonyl, sulfonate, sulfonamino, and sulfonamido.

In a second aspect, the invention relates to a compound of formula (II)

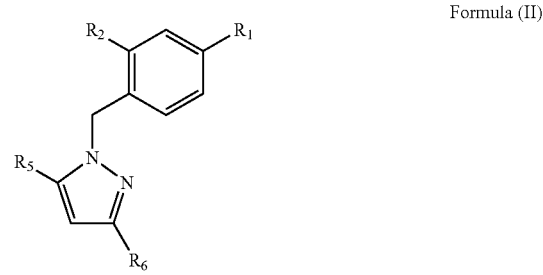

Formula (II)

wherein
R1 and R2 are identical or different and are independently chosen among hydrogen, hydroxyl, halogen, haloalkyl, alkyl, aryl, arylalkyl, nitro, cyano, amino, alkoxy, alkoxyalkyl, heteroaryl, cycloalkyl and heterocyclyl; and R5 and R6 are identical or different and are independently chosen among ester, substituted or non-substituted alkyloxycarbonyl preferably a substituted or non-substituted C1-C6 alkyloxycarbonyl, halogen, haloalkyl, alkyl, aryl, arylalkyl, nitro, cyano, amino, alkoxy, alkoxyalkyl, heteroaryl, cycloalkyl, heterocyclyl, boronate, phosphate, phosphonate, sulfinyl, sulfonyl, sulfonate, sulfonamino, and sulfonamido.

In a third aspect, the invention relates to a pharmaceutical composition comprising at least one agent or one compound as defined herein.

In a fourth aspect, the invention relates to an agent of formula (I) as described above or a compound of formula (II) as described above, and a further antiviral agent as a combined preparation for simultaneous, separate or sequential use in the treatment or prophylaxis of respiratory syncytial virus infection, wherein said further antiviral agent is selected from the group consisting of acyclovir, cidofovir, docosanol, famciclovir, foscarnet, fomivirsen, ganciclovir, idoxuridine, penciclovir, peramivir, trifluridine, valacyclovir, vidarabine, lamivudine, and ribavirin.

DETAILED DESCRIPTION OF THE INVENTION

Agent for Use in a Method for Treating Infection by RSV
Respiratory Syncytial Virus (RSV) is an enveloped, non-segmented negative-strand RNA virus that belongs to the Pneumovirus genus, Pneumovirinae subfamily, Paramyxoviridae family, Mononegavirales order. As for all Mononegavirales, the genomic RNA of RSV is tightly bound to the viral nucleoprotein (N) and maintained as a left-handed helical N-RNA ribonucleoprotein (RNP) complex. The structure of a RNP-like particle consisting of N bound to RNA was solved (PDB 4BKK). The RNP serves as a template for transcription and replication by the RNA-dependent RNA polymerase complex (RdRp), consisting of the catalytic subunit L (large protein) and its cofactor P (phosphoprotein). The RSV N, P, and L proteins are sufficient to allow viral RNA replication. The neo-synthesized genomic and anti-genomic RNAs are encapsidated by N as they are synthesized. There is no equivalent to the RSV RdRp in the host cell.

Efficient viral transcription requires L, P and the transcription processivity cofactor M2-1, whose structure has been resolved (PDB 2I8B and 4C3E). The inventors concentrated their efforts on the efficient and specific recognition of the RNP template by the RdRp, which proved to be critical for viral replication and transcription. RSV P protein is an essential polymerase cofactor that is capable of interacting with multiple partners. P is a modular protein consisting of a central Oligomerization Domain (P-OD, aa 121 to 160), flanked by two long Intrinsically Disordered Regions (IDR) P-NTD (aa 1 to 120) and P-CTD (aa 161 to 241). P forms homo-tetramers and binds to L, N and M2-1. Using these properties, P positions the RdRp complex on the RNP template and is probably involved in translocation of the RdRp along the nucleocapsid. P is also believed to act as a chaperone, maintaining newly synthesized N in a soluble form (N0) and delivering it to the neo-synthesized genomic and antigenomic RNAs for encapsidation. P thus acts as a hub that promotes multiple but highly specific protein:protein interactions, and perturbing these interactions could be a new approach for drug development. Among these interactions, the inventors found out that P:N interactions, and in particular the P:RNP interaction, constitute targets of choice for small molecule inhibitors. Thus, characterization of the P-RNP interaction at the molecular level is of main interest.

The inventors have thus used the binding site on N of the two carboxy terminal residues of P, namely aspartate-phenylalanine (Asp-Phe), as a target for rational design of potential inhibitors of the P-RNP interactions. Indeed, this well-defined site has a crucial role for P binding and is composed of residues with high sequence conservation. Based on X-ray crystal structures of the N-terminal domain of N (N-NTD, aa 31-252) in complex with a Asp-Phe dipeptide or a phenylalanine and a sulfate molecule in place of a carboxyl group of Asp, the inventors screened the ZINC database for compounds that share with Phe an aromatic ring to be buried in the hydrophobic pocket of N-NTD with further stabilization by electrostatic interactions. The screening by AUTODOCK generated a set of approximately 1500 ranked compounds.

The set was reduced to approximately 300 compounds by restricting the molecular weight to be lower than 350 g/mol. Compounds of this set were ordered based on the interaction energy between the ligand and the protein N and the best 50 compounds were selected for further experimental studies.

After fastidious studies including X-ray crystallography, nuclear magnetic resonance, isothermal titration calorimetry and surface plasmon resonance, the inventors found out a specific class of compounds which shows unexpected and highly promising therapeutic property.

Thus, in a first aspect, the invention relates to an agent for use for treating an infection by respiratory syncytial virus (RSV), wherein said agent is represented in formula (I):

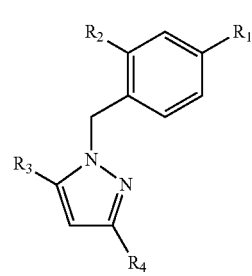

Formula (I)

wherein:
R1 and R2 are identical or different and are independently chosen among hydrogen, halogen, hydroxyl, haloalkyl, alkyl, aryl, arylalkyl, nitro, cyano, amino, alkoxy, alkoxyalkyl, heteroaryl, cycloalkyl and heterocyclyl; and
R3 and R4 are identical or different and are independently chosen among carboxylate, ester, substituted or non-substituted alkyloxycarbonyl, halogen, haloalkyl, alkyl, aryl, arylalkyl, nitro, cyano, amino, alkoxy, alkoxyalkyl, heteroaryl, cycloalkyl, heterocyclyl, boronate, phosphate, phosphonate, sulfinyl, sulfonyl, sulfonate, sulfonamino, sulfonamido.

In a preferred embodiment, R1 and R2 are identical or different and are independently chosen among hydrogen, halogen, hydroxyl, nitro, cyano, amino, and alkoxy.

More preferably, R1 and R2 are identical or different and are independently chosen among hydrogen, halogen, nitro, cyano, and amino. Even more preferably, R1 and R2 are identical or different and are independently chosen among hydrogen and halogen.

In a preferred embodiment, R3 and R4 are identical or different and are independently chosen among carboxylate and substituted or non-substituted alkyloxycarbonyl. Said substituted or non-substituted alkyloxycarbonyl is preferably a substituted or non-substituted C1-C6 alkyloxycarbonyl.

Typically, said agent is an antiviral agent, i.e. an inhibitor of viral replication. The term "antiviral agent," as used herein, refers to an agent that is effective to inhibit the formation of viral particles and/or the viral replication and/or the viral transcription of RSV in a subject. Preferably, the antiviral agent of the present invention is effective in inactivating the interaction between the phosphoprotein P and the nucleoprotein N/RNP complex.

The agent of the invention is used for treating a subject. As used herein, the term "subject" denotes a mammal, such as a human, a bovine subject, an ovine, an equine, a porcine, a rodent, a feline, a canine, or a primate. Preferably, a subject according to the invention is a human.

Very closely related forms of human RSV exist for other mammals like sheep and cattle. The most prominent is bovine Respiratory Syncytial Virus (BRSV) that is the most important viral respiratory pathogen of calves. BRSV provokes high mortality rates (2-20%) due to pneumonia and related illnesses and thus accounts for large economic losses in dairy and beef farming.

Consequently, in the context of the invention, the RSV may be a human strain of RSV, a bovine strain of RSV, an ovine strain of RSV, an equine strain of RSV, a porcine strain of RSV, a rodent strain of RSV, a feline strain of RSV, a canine strain of RSV, or a primate strain of RSV.

As used herein, the terms "agent of formula (I)" or "agent of the invention" are meant to include any compound of formula (I), as well as their salts, solvates, and stereoisomers. The agents of the invention are intended to be used as antiviral agents directed against RSV.

The term "ester" refers to a functional group —COO—R where R is an alkyl having 1 to 10 carbon atoms. Preferably, said ester is a substituted or a non-substituted alkyloxycarbonyl. Preferably, said ester is with carboxyl C attached to the pyrazole ring. More preferably, said ester is an alkyl-, aryl-, arylalkyl-, haloalkyl-, aminoalkyl-, alkoxy-, alkoxyalkyl-, heteroaryl-, cycloalkyl-, heterocyclyl-ester. Preferably, the alkyloxycarbonyl according to the invention is a C1-C6 alkyloxycarbonyl. Said alkyloxycarbonyl may be substituted or non-substituted.

The term "substituents" refers to a group "substituted" on an alkyl, alkenyl, alkynyl, cycloalkyl, heterocycle, aryl, arylalkyl, heteroaryl or heteroarylalkyl group at any atom of that group. Suitable substituents include, without limitation: acyl, acylamido, acyloxy, alkoxy, alkyl, alkenyl, alkynyl, amido, amino, carboxy, cyano, ester, halo, hydroxy, imino, nitro, oxo, phosphonate, sulfinyl, sulfonyl, sulfonate, sulfonamino, sulfonamido, thioamido, thiol, thioxo, and ureido.

Preferably, the C1-C6 alkyloxycarbonyl of the invention is substituted with a substituent chosen among acyl, acyloxy, alkoxy, or carboxy.

The term "haloalkyl" refers to a functional group alkyl having 1 to 10 carbon atoms, and substituted by at least a halogen, preferably 1 to 5 carbon atoms.

The term "alkyl" refers to a linear or branched alkyl functional group having 1 to 10 carbon atoms.

The term "aryl" refers to a phenyl, naphtylradical.

The term "arylalkyl" refers to an alkyl group linked to an aryl.

The term "alkoxy" refers to a group R'—O—, where R' is a C1-10 alkyl.

The term "alkoxyalkyl" refers to a group R'—O—R"—, where R' and R" are each independently a C1-10 alkyl, preferably R" a C1-3 alkyl.

The term "heteroaryl" refers to a heteroaromatic group, preferably chosen from pyrrolyl, furanyl, thiophenyl, imidazolyl, pyrazolyl, thiazolyl, oxazolyl, thienyl, indolyl, purine, or pyrimidine.

The term "cycloalkyl" refers to a group derived from a cycloalkane comprising 1 to 10 carbon atoms.

The term "heterocyclyl" refers to a saturated ring comprising at least a heteroatom.

As used herein, the term "halogen" preferably refers to a chemical element selected from the group consisting of: fluorine (F), chlorine (Cl), bromine (Br), and iodine (I).

Thus, in one embodiment, the invention relates to an agent for use for treating an infection by respiratory syncytial virus (RSV), wherein said agent is represented in formula (I); and R1 and R2 are identical or different and are independently chosen among hydrogen and halogen such as fluorine (F), chlorine (Cl), bromine (Br), and iodine (I); and R3 and R4 are identical or different and are carboxylate.

Preferably, R1 and R2 are identical or different and are independently chosen among fluorine, chlorine, bromine and iodine. More preferably, R1 and R2 are identical or different and are independently chosen among chlorine, bromine and iodine.

Preferably, R3 and R4 are identical and are both carboxylate. Thus, in this preferred embodiment, the agent of the invention is represented in Formula (Ia) as follows:

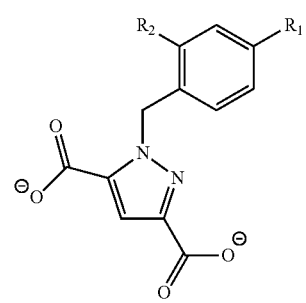

Formula (Ia)

In a preferred embodiment, R3 and R4 are identical and are both carboxylate and R1 and R2 are identical and are both hydrogen. Thus, in this preferred embodiment, the agent of the invention is represented in Formula (Ib) as follows:

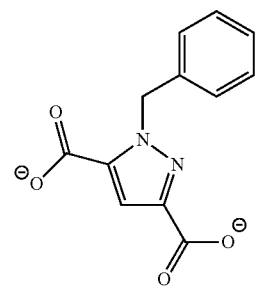

Formula (Ib)

The agent of formula (Ib) is also called 1-(Benzyl)-pyrazole-3,5-dicarboxylate or M61. M61 is referenced as ZINC02519565 in the ZINC database. It is available from Sigma-Aldrich (Sigma-Aldrich Chemie S.a.r.l., L'Isle d'Abeau Chesnes, 38297 Saint-Quentin Fallavier, France) with the reference L166170.

In a preferred embodiment, R3 and R4 are identical and are both carboxylate, R1 is fluorine and R2 is hydrogen. Thus, in this preferred embodiment, the agent of the invention is represented in Formula (Ic) as follows:

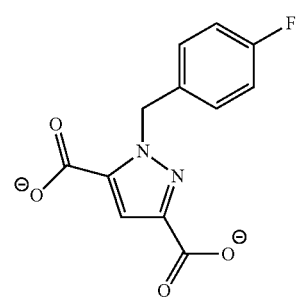

Formula (Ic)

The agent of formula (Ic) is also called 1-(4-fluoroBenzyl)-pyrazole-3,5-dicarboxylate or M72. M72 is referenced as ZINC04858137 in the ZINC database. It is available from Mcule (Mcule, Inc., Fehervari ut 130, 1116, Budapest, Hungary) (reference MCULE-1942132126), from Ambinter (Ambinter c/o Greenpharma, 3, allée du titane 45100 Orléans, FRANCE) (reference Amb8617637) and ChemBridge (ChemBridge Corporation, 11199 Sorrento Valley Road, Suite 206, San Diego, Calif., 92121, USA) (reference 9002906).

In a preferred embodiment, R3 and R4 are identical and are both carboxylate, R1 is bromine and R2 is hydrogen. Thus, in this preferred embodiment, the agent of the invention is represented in Formula (Id) as follows:

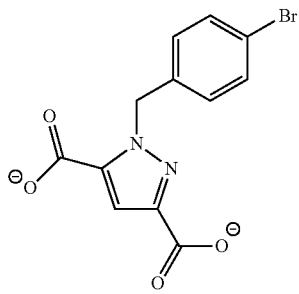

Formula (Id)

The agent of formula (Id) is also called 1-(4-bromoBenzyl)-pyrazole-3,5-dicarboxylate or M68. M68 is referenced as ZINC04852697 in the ZINC database. It is available from eMolecules (eMolecules, 11025 N. Torrey Pines Rd, Suite 140 La Jolla, Calif. 92037, USA) (reference 2321388), Molport (Molport, SIA MolPort, Lacplesa 41, Riga, LV-1011, Latvia) (reference MolPort-002-127-359), Mcule (reference MCULE-3092041599), Ambinter (reference Amb8617078) and ChemBridge (reference 7998757).

In a preferred embodiment, R3 and R4 are identical and are both carboxylate, R1 is hydrogen and R2 is chlorine. Thus, in this preferred embodiment, the agent of the invention is represented in Formula (Ie) as follows:

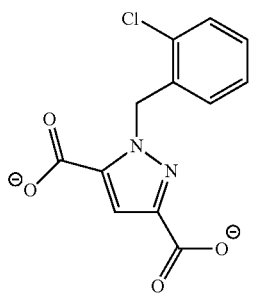

Formula (Ie)

The agent of formula (Ie) is also called 1-(2-chloroBenzyl)-pyrazole-3,5-dicarboxylate or M81. M81 is referenced as ZINC04856082 in the ZINC database.

It is available from Mcule (reference MCULE-6589630849), Ambinter (reference Amb8617276) and from ChemBridge (reference 9000194).

In a preferred embodiment, R3 and R4 are identical and are both carboxylate and R1 and R2 are identical and are both chlorine.

Thus, in this preferred embodiment, the agent of the invention is represented in Formula (If) as follows:

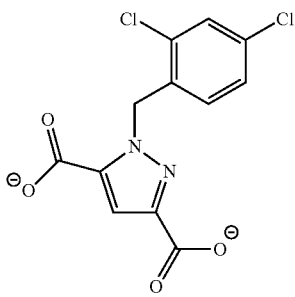

Formula (If)

The agent of formula (If) is also called 1-(2,4-dichloroBenzyl)-pyrazole-3,5-dicarboxylate or M76. M76 is referenced as ZINC04808502 in the ZINC database.

It is available from Mcule (reference MCULE-2289244094), from Ambinter (reference Amb8610738) and from ChemBridge (reference 7953989).

The inventors have shown that compound M76 showed an enhanced affinity for N-D, reflecting an enhanced antiviral activity.

In a preferred embodiment, the agent for use according to the invention is selected from the group consisting of M61, M72, M68, M81 and M76, which are respectively shown in formulas (Ib), (Ic), (Id), (Ie), (If).

Compound of the Invention

The inventors found out that it may be convenient or desirable to prepare, purify, and/or handle the agents of the invention in a chemically protected form.

Preferably, said new compounds are modified and chemically protected forms of the agents of the invention of formula (I).

The term "chemically protected form" is used herein in the conventional chemical sense and pertains to a compound in which one or more reactive functional groups are protected from undesirable chemical reactions under specified conditions (e.g., pH, temperature, radiation, solvent, and the like).

Reversible chemical protection is also desirable to screen charges that are important for molecular recognition, but incompatible with an hydrophobic environment, and that can be released when the protected form is converted to its active form through a metabolic process in vivo.

In practice, well known chemical methods are employed to reversibly render unreactive a functional group, which otherwise would be reactive, under specified conditions.

In a chemically protected form, one or more reactive functional groups are in the form of a protected or protecting group (also known as a masked or masking group or a blocked or blocking group).

By protecting a reactive functional group, reactions involving other unprotected reactive functional groups can be performed, without affecting the protected group; the protecting group may be removed, usually in a subsequent step, without substantially affecting the remainder of the molecule.

A wide variety of such "protecting," "blocking," or "masking" methods are widely used and well known in organic synthesis. Typically, a hydroxyl group may be protected as an ether (—OR) or an ester (—OC(O)R), for example, as: a t-butyl ether; a benzyl, benzhydryl (diphenylmethyl), or trityl(triphenylmethyl) ether; a trimethylsilyl or t-butyldimethylsilyl ether; or an acetyl ester (—OC(O)CH3, —OAc).

Thus, in a second aspect, the invention relates to a compound of formula (II)

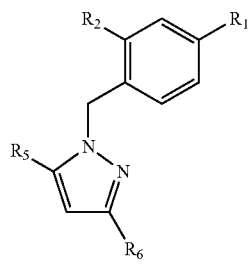

Formula (II)

wherein:
R1 and R2 are identical or different and are independently chosen among hydrogen, hydroxyl, halogen, haloalkyl, alkyl, aryl, arylalkyl, nitro, cyano, amino, alkoxy, alkoxyalkyl heteroaryl, cycloalkyl and heterocyclyl; and
R5 and R6 are identical or different and are independently chosen among ester, substituted or non-substituted alkyloxycarbonyl halogen, haloalkyl, alkyl, aryl, arylalkyl, nitro, cyano, amino, alkoxy, alkoxyalkyl, heteroaryl, cycloalkyl, heterocyclyl, boronate, phosphate, phosphonate, sulfinyl, sulfonyl, sulfonate, sulfonamino, and sulfonamido.

The above definitions of the different functional groups are usable here.

In a preferred embodiment, R1 and R2 are identical or different and are independently chosen among hydrogen, halogen, hydroxyl, nitro, cyano, amino, and alkoxy.

More preferably, R1 and R2 are identical or different and are independently chosen among hydrogen, halogen, nitro, cyano, and amino.

Even more preferably, R1 and R2 are identical or different and are independently chosen among hydrogen and halogen.

In a preferred embodiment, R5 and R6 are identical or different and are independently chosen among substituted or non-substituted alkyloxycarbonyl, preferably substituted or non-substituted C1-C6 alkyloxycarbonyl, halogen, haloalkyl, alkyl, aryl, arylalkyl, alkoxy, alkoxyalkyl, heteroaryl, cycloalkyl, heterocyclyl, (alkanoyloxy)alkoxy]carbonyl.

In a more preferred embodiment, R5 and R6 are identical or different and are independently chosen among substituted or non-substituted alkyloxycarbonyl, preferably substituted or non-substituted C1-C6 alkyloxycarbonyl.

In a more preferred embodiment, R5 and R6 are identical and are both —CO2CH2OCOCH3.

As used herein, the expression "compounds of formula (II)" or "compounds of the invention" are meant to include the compounds of general formula (II), as well as their salts, solvates, and stereoisomers. In a preferred embodiment, the compounds of formula (II) are prodrugs. As used herein, the term "prodrug" refers to a compound which upon administration to a subject in need thereof undergoes cleavage in vivo either by enzymatic or chemical processes to release its active metabolite. Typically, prodrugs have the same mechanism of action as their active metabolites.

Typically, R5 and R6 do not represent a carboxylate group.

Preferably, R1 and R2 are independently halogens.

In a more preferred embodiment, R1 and R2 are identical and are both iodine. Preferably, said compound is as represented in formula (III):

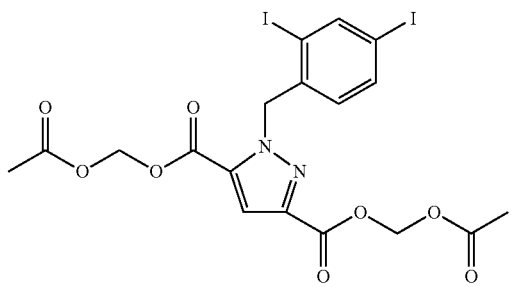

Formula (III)

In another embodiment, R1 and R2 are identical and are both chlorine. In this embodiment, said compound is as represented in formula (IV):

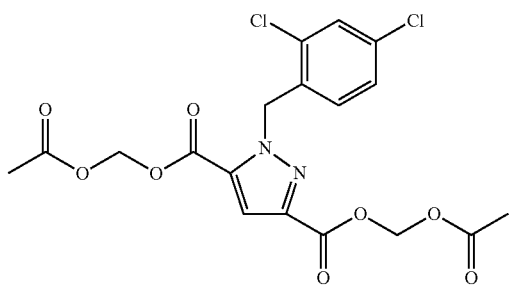

Formula (IV)

The compound of formula IV is also called M76b.

In a third aspect, the invention relates to the compound of the invention for use in therapy. Preferably, the invention relates to the use of the compound of the invention for use as an antiviral agent, more preferably for use as an antiviral agent directed against RSV.

Pharmaceutical Composition

In a fourth aspect, the invention relates to pharmaceutical composition comprising at least one agent or one compound of the invention. The agent of the invention or the compound of the invention as above described may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce an adverse, allergic or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, intranasal, intraocular, intravenous, intramuscular or subcutaneous administration and the like. Preferably, the pharmaceutical compositions of the invention can be formulated for an intranasal administration.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment. It will be appreciated that appropriate dosages of the agents and compounds, and compositions comprising the compounds, can vary from patient to patient. Determining the optimal dosage will generally involve the balancing of the level of therapeutic benefit against any risk or deleterious side effects of the treatments described herein.

The selected dosage level will depend on a variety of factors including, but not limited to, the activity of the particular compound, the route of administration, the time of administration, the rate of excretion of the compound, the duration of the treatment, other drugs, compounds, and/or materials used in combination, and the age, sex, weight, condition, general health, and prior medical history of the patient. The amount of compound and route of administration will ultimately be at the discretion of the physician, although generally the dosage will be to achieve local concentrations at the site of action which achieve the desired effect without causing substantial harmful or deleterious side-effects.

To prepare pharmaceutical compositions, an effective amount of the compound of the invention may be dissolved or dispersed in a pharmaceutically acceptable carrier or aqueous medium. In one embodiment, the agent or compound of the invention is administered to a patient in an amount sufficient to treat RSV infection. An amount adequate to accomplish this is defined as "therapeutically effective dose". Amounts effective for this use will depend on, for example, the particular agent or compound employed, the route of administration, the weight and general state of health of the patient, and the judgement of the prescribing physician.

For example, an amount of the compound of the invention falling within the range of a 100 ng to 10 mg dose given intranasally once a day (e.g., in the evening) would be a therapeutically effective amount.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, mixtures thereof and in oils. Under ordinary conditions of storage and use, these preparations contain a preservative to prevent the growth of microorganisms.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution may be suitably buffered and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

In addition to the compounds formulated for parenteral administration, such as intravenous or intramuscular injection, other pharmaceutically acceptable forms include, e.g. tablets or other solids for oral administration; time release capsules; and any other form currently used.

For aerosol administration, the agent or compound of the invention is preferably supplied in finely divided from along with a surfactant and propellant. The surfactant must, of course, be nontoxic, and preferably soluble in the propellant. Representative of such agents are the esters or partial esters of fatty acids containing from 6 to 22 carbon atoms, such as caproic, octanoic lauric, palmitic, stearic, linoleic, linolenic, olesteric and oleic acids with an aliphatic polyhydric alcohol or its cyclic anhydride. Mixed esters, such as mixed or natural glycerides may be employed. A carrier can also be included, as desired, as with, e.g., lecithin for intranasal delivery. An example includes a solution in which each milliliter included 7.5 mg NaCl, 1.7 mg citric acid monohydrate, 3 mg disodium phosphate dihydrate and 0.2 mg benzalkonium chloride solution (50%) (Gozes et al., J Mol Neurosci. 19(1-2):167-70 (2002)).

Finally, the agents or the compounds of the invention can be formulated with a further antiviral agent. Examples of further antiviral agents include, but are not limited to viral maturation inhibitors, agents gene replication, iRNA agents, antisense RNA, vectors expressing iRNA agents or antisense RNA, and antiviral antibodies. Preferably, said antiviral agent is directed against respiratory syncytial virus includes, but are not limited to acyclovir, cidofovir, docosanol, famciclovir, foscarnet, fomivirsen, ganciclovir, idoxuridine, penciclovir, peramivir, trifluridine, valacyclovir, vidarabine, lamivudine, and ribavirin. Preferably, said further agent is ribavirin.

In a specific embodiment, the invention relates to said pharmaceutical composition for use in therapy, preferably for treating a respiratory syncytial virus infection.

In a fifth aspect, the invention relates to an agent of formula (I) as described above or a compound of formula (II) or (III) as described above, and a further antiviral agent as a combined preparation for simultaneous, separate or sequential use in the treatment or prophylaxis of respiratory syncytial virus infection, wherein said further antiviral agent is selected from the group consisting of acyclovir, cidofovir, docosanol, famciclovir, foscarnet, fomivirsen, ganciclovir, idoxuridine, penciclovir, peramivir, trifluridine, valacyclovir, vidarabine, lamivudine, and ribavirin. Preferably, said further antiviral agent is ribavirin.

Methods of Use

The methods described herein include methods of treating a respiratory syncytial virus infection in a subject in need of treatment, comprising administering to the subject a therapeutically effective amount of a compound described herein, such as an agent of formula (I) or a compound of formula (II) or (III).

Also described herein are methods inhibiting replication of respiratory syncytial virus, comprising contacting a sample comprising respiratory syncytial virus with an effective amount of an agent or compound described herein.

The invention will be further illustrated by the following examples. However, these examples should not be interpreted in any way as limiting the scope of the present invention.

EXAMPLE

Example 1

Agents Inactivating the Interaction Between the Phosphoprotein P and the Nucleoprotein in the RNP:P Complex of RSV Introduction In this study, the inventors investigated N-NTD:P-CTD interaction.

First, they crystallized N-NTD alone, in complex with C-terminal peptides of P, or with a single phenylalanine. The phenylalanine equivalent to P:F241 is deeply buried in a conserved pocket of N-NTD, interacting with all critical residues previously identified. The molecular models of the complexes associated with N-NTD provided the starting structure used to screen compounds from the ZINC database. The screening procedure and further calculations identified the 50 best molecules that were selected for further experimental studies. NMR experiments with $^{15}$N labeled N-NTD yielded contact regions and binding affinities for several of these compounds.

The best derivatives were 1-Benzyl-1H-Pyrazole-3,5-di-Carboxylates (BPdC) that showed micromolar range affinities for N-NTD, depending on the halogen substituents on the benzyl ring. Isothermal titration calorimetry (ITC) was used to further characterize their binding properties and surface plasmon resonance (SPR) investigated their competition with N-NTD:P-CTD association. Crystal structures of N-NTD in complex with three BPdCs, bearing alternative benzyl cycle substitutions, were obtained at 2.0, 2.7 and 2.9 Å resolution, respectively.

Altogether, the results of the inventors demonstrate that this family of compounds constitutes an excellent lead for drug development.

Materials & Methods

Plasmids

The pGEX-P-CTD plasmid containing the sequence of P C-terminal region (P-CTD, residues 161 to 241) has been described previously (Castagne et al. 2004)(Tran et al. 2007b). The pET-N[31-252] plasmid encoding the N N-terminal region (N-NTD, residues 31 to 252) with a C-terminal poly-His tag has been described previously (Galloux et al., 2012).

Expression and Purification of Recombinant Proteins

*E. coli* BL21(DE3) bacteria (Novagen, Madison, Wis.) transformed pGEX-P-CTD, pET-N[31-252] or were grown at 37° C. for 8 hours in 100 ml of Luria Bertani (LB) medium containing either 100 µg/ml ampicillin or 50 µg/ml of kanamycine respectively. The same volume of LB was then added and protein expression was induced by adding 80 µg/ml isopropyl-B-D-thio-galactoside (IPTG) to the medium. The bacteria were incubated for 15 hours at 28° C. and then harvested by centrifugation. For GST-fusion protein purification, bacterial pellets were re-suspended in lysis buffer (50 mM Tris-HCl pH 7.8, 60 mM NaCl, 1 mM EDTA, 2 mM DTT, 0.2% Triton X-100, 1 mg/ml lysozyme) supplemented with complete protease inhibitor cocktail (Roche, Mannheim, Germany) and incubated for 1 hour on ice, sonicated, and centrifuged at 4° C. for 30 min at 10,000×g. Glutathione-Sepharose 4B beads (GE Healthcare, Uppsala, Sweden) were added to clarified supernatants and incubated at 4° C. for 15 hours. Beads were then washed two times in lysis buffer and three times in PBS 1X, then stored at 4° C. in an equal volume of PBS. For poly-His fusion protein purification, bacterial pellets were re-suspended in lysis buffer (20 mM Tris-HCl pH8, 500 mM NaCl, 0.1% TritonX-100, 10 mM imidazole, 1 mg/ml lysozyme) supplemented with complete protease inhibitor cocktail (Roche). After sonication and centrifugation, lysates were incubated 1 hour with chelating Sepharose Fast Flow beads charged with Ni$^{2+}$ (GE Healthcare). Finally, beads were successively washed in the washing buffer (20 mM Tris-HCl, pH 8, 500 mM NaCl) containing crescent concentration of imidazole (25, 50, and 100 mM), and proteins were eluted in the same buffer with 800 mM imidazole. The C-terminal His tag was not removed for crystallization trials.

N-NTD samples uniformly labeled with stable isotopes for NMR measurements were produced in minimal M9 medium supplemented with 1 g/L $^{15}$NH4Cl and 3 g/L unlabeled or $^{13}$C-glucose. The protocols were adapted from rich medium: an initial preculture of 15 mL in LB medium was used to inoculate a 500 mL M9 culture grown to saturation, and 500 mL of fresh M9 medium were added before induction. Purification was carried out as described above and followed by a final dialysis step to exchange the sample into NMR buffer (20 mM MES pH 6.5, 250 mM NaCl, 1.5 mM TCEP). A U-$^{13}$C, $^{15}$N, 70%-$^{2}$H labeled N-NTD sample was prepared by starting from a 100 mL preculture in LB medium, used to inoculate 1 L of unlabeled M9. Cells were harvested at OD600=0.6 and transferred into 100 mL of $^{2}$H-M9 medium prepared with 95% $^{2}$H$_2$O. After 1 h at 37° C., cells were harvested again by centrifugation and transferred into 900 mL $^{2}$H-M9 medium. Induction was started after 1 h and carried out at 28° C. overnight.

Crystallization and Diffraction Data Collection

A N-NTD solution was concentrated to 8 mg/ml in 20 mM Tris/HCl pH 7.5, NaCl 50 mM. A nanoscale robot crystallization screen was performed in 96 well, sitting drop plates at 18° C. Crystals were observed under several conditions. After optimization the best crystals were obtained in 25% Peg4K or 28% Peg5000MME. with 100 mM Hepes pH 7.5 buffer and 200 mM Ammonium sulfate. Diffraction quality crystals were grown by hanging-drop and transferred in a solution containing 30% Peg4000 or Peg5000MME plus 5% glycerol and 5% Peg400 and flash-frozen under liquid nitrogen.

Structure Determination

X-ray diffraction data were collected at the beamline PX06-SA at the SLS, PROXIMA-1 at Soleil and ID14-4 at the ESRF. Data were processed using the XDS package (Kabsch 2010) and scaled with SCALA (Evans 2006). The structure was solved by molecular replacement with PHASER (McCoy A. J. et al, 2007) using PDB entry 2wj8 as search model. Subsequently, careful model building with COOT (Emsley, Lohkamp et al. 2010) alternated with crystallographic refinement with program BUSTER/TNT (Blanc et al., 2004), which included NCS restraints and TLS refinement. For BPdC derivatives stereochemical restraint dictionaries were generated with the Grade Web Server (ref). In addition, target restraints using M76 molecular model were used for the refinement of P3, P7, M81 and M72 models.

Drug Design

The X-ray structure of the N-NTD complexed with P2 was used as a starting configuration. The missing 3D coordinates were added using the SWISS-MODEL package. Using the relative position of the phenylalanine of P2 and the sulfate ion found in the N-P2 complex a docking volume was defined using AUTODOCK vina (O. Trott & A J Olson, AutoDock Vina J. Comput Chem 2010 31:455-461.à By virtual screening of the Zinc database (Irwin 2012) compounds were selected on the basis of the following requirements: (&) fit in the defined volume; (ii) possess an aromatic moiety as F241; (iii) target R150 of N-NTD mimicking the carboxylate backbone of F241; (iv) target R132 of N-NTD replacing the interactions of this residue with sulfate ion. The initial screening identified 1500 compounds, further reduced to 300 by elimination of those with molecular weights higher than 350 and those with potential toxicity. Compounds of this reduced set were ordered based on favorable van der Waals interaction energies between the ligand and N-NTD. The best 100 compounds were energy minimized and ordered with a free energy scoring function. Here the atoms of N-NTD located within 8 Å to the ligand were left to adopt a relaxed conformation while the atoms of the rest of the protein were harmonically restrained to their initial positions. The best 50 compounds were used for experimental testing.

Nuclear Magnetic Resonance

Backbone assignment of N-NTD was based on the acquisition of standard triple resonance NMR experiments (HNCO, HNCA, HN(CO)CA, CBCA(CO)NH, HNCACB) on a 600 MHz Bruker Avance III spectrometer equipped with a cryogenic TCI probe, using triply U-$^{13}$C, U-$^{15}$N, 70%-$^{2}$H labeled N-NTD. Typical NMR samples contained 185 µL N-NTD with concentrations between 80 and 200 µM and 15 µL $^{2}$H$_2$O in a 3 mm tube. Due to slow deuteron to proton exchange in several highly exchange-protected regions, this data set was completed by acquiring HNCO and HNCA spectra of doubly U-$^{13}$C,U-$^{15}$N labeled N-NTD. Spectra were processed with Topspin 3.1 and NmrPipe (Delaglio et al. 1995). Analysis of NMR experiments was performed in CCPNMR (Vranken et al. 2005).

Chemical shift perturbation (CSP) experiments were carried out with 50 µM U-$^{15}$N labeled N-NTD on a 700 MHz Bruker Avance III spectrometer equipped with a TXI probe by adding increasing amounts of M61, M68, M72, M76 and M81 from concentrated stock solutions (25, 10 or 5 mM) in ethanol. Titrations were completed by measuring $^{1}$H, $^{15}$N-HSQC spectra with a constant total protein concentration and molar ligand:protein ratios, r, between 0.25:1 and 20:1. Dissociation constants were determined for a given residue, assuming a two-site fast exchange model with a 1:1 stoichiometry, by fitting the chemical shift difference ($\delta - \delta_{free}$) as a function of molar ratios in Origin 7 software (OriginLab).

$$\delta - \delta_{free} = \alpha * (\delta_{bound} - \delta_{free}) = B * \left( A + r - \sqrt{(A+r)^2 - 4r} \right),$$

with $$B = \frac{1}{2}(\delta_{bound} - \delta_{free}) \text{ and } K_d = (A - 1) * [N - NTD]_{tot}.$$

Combined $^{1}$H and $^{15}$N CSPs were calculated from:

$$\Delta\delta^1 H^{15} N = \sqrt{(\delta_{1H} - \delta_{1H}^{free})^2 + (\delta_{15N} - \delta_{15N}^{free})^2 / 100}.$$

All chemical shifts were corrected for the perturbations induced by ethanol by using a spectrum obtained with a sample of N-NTD with 5 µL ethanol and by assuming a linear relationship between these perturbations and the added volumes of ligand solutions.

Surface Plasmon Resonance Competition Assays

The assays were carried out at 25° C. in a buffer 20 mM TrisHCl, pH 8, 150 mM NaCl.

A goat anti-GST antibody (Biacore GST Capture Kit) was covalently coupled to a CMS sensorchip, using a Biacore 2000 instrument and the Amine Coupling Kit (GE Healthcare), reaching an immobilization density of around 10000 resonance units (RU; 1RU≈1 pg.mm-2). This surface was used to capture tightly GST-fused P-CTD to a density of 1200-1300 RU, or GST (800 RU) as a control. N-NTD (20 µM), alone or mixed and equilibrated for over 2 hours with the different inhibitor candidates (concentration range: 5-750 µM), was then injected over the GST-P-CTD and GST surfaces for one minute at a flow rate of 50 ml/min. After each injection, the interaction buffer was flowed on the surface until all the N-NTD molecules dissociated (taking advantage of the transient nature of the N-NTD/P-CTD interaction). At the end of the series, the surfaces were regenerated with a 2-min 10 mM glycine-HCl (pH 1.5) wash and two 1-min washes with 0.05% SDS and 20 mM NaOH. The real-time interaction profiles were double referenced using the Scrubber 2.0 software (BioLogic Software), that is both the signals from the reference surface (with GST captured on the anti-GST antibody) and from blank experiments using the compounds alone were subtracted. The steady-state SPR responses (Req) were plotted against the compound concentration C and fitted using the BIAevaluation 4.1 software (GE Healthcare), according to the following equation:

$$\left(\frac{Req}{R_0}\right)*\lfloor Ncore\rfloor = \left(\frac{\lfloor Ncore\rfloor - C - K_i}{2}\right) + \sqrt{\left(\frac{\lfloor Ncore\rfloor + C + K_i}{4}\right)(2 - \lfloor Ncore\rfloor * C)}$$

where is the concentration of N-NTD (20 μM) and R0 the steady-state SPR response for N-NTD alone, allowing to determine the inhibition constants Ki for each compound.

Isothermal Titration Calorimetry

ITC experiments were performed using the high precision VP-ITC system (MicroCal, GE Healthcare) and quantified with the Origin7 software provided by the manufacturer. All molecules were dissolved in 20 mM Tris-HCl, pH 8, 150 mM NaCl, 5% Ethanol and the binding enthalpies were measured by injecting the M76 or M61 solutions at 1.5 mM into calorimetric cell containing 30 μM N-NTD solution. Titrations were performed at 18° C. with 7 μl injections of M76 or M61 ligands every 350s. Heat signals were corrected for the heats of dilution and normalized to the amount of compound injected. Binding stoichiometries, enthalpy values and equilibrium dissociation constants were determined by fitting the corrected data to a 1:1 interaction model using the Origin7 software (OriginLab).

Results

Structure of Isolated N-NTD

It was recently shown that recombinant His-tagged N-NTD (residues 31-252 of N), the minimal domain of interaction with P-CTD, is monomeric and mainly of helical content, consistent with the crystal structure of N-RNA rings (PDB 2WJ8). Based on these data, the inventors first attempted crystallizing this domain alone. Recombinant His-tagged N-NTD was produced as previously described. N-NTD globular domain was crystallized in 2 different primitive orthorhombic space groups at 2.1 and 2.4 Å resolution for Nat1 and Nat2 with two independent molecules in each crystal form. Structure of the isolated globular domain is essentially identical to that observed within the ribonucleoprotein complex and variations are restricted to surface loops of N-NTD involved in N-N lateral contact or in N-RNA interactions in the RNP context. This includes the αN7-αN8 loop which bears R234 involved in key interactions for lateral N-N contacts in the RNP, the αN3-αN4 loop which bears K170 interacting with the RNA chain, and D175 which establishes a salt bridge with R338 located in the C-terminal domain of N that closes the RNA groove. Other structural variations are observed in protruding regions, located on the structurally variable segment within the N-NTD of Mononegavirales and at the opposite side of RNA binding region, the β-hairpin and αI2-η1 loop. The two latter loops in the RNP context already have a high flexibility as revealed by their refined b-factor values in this molecular model. Overall, these data show that N polymerization and RNA binding required to RNP assembly do not involve large rearrangements of N-terminal domain other than the adaptation of specific loops.

Structural Characterization of P-CTD Binding on N-NTD

N-NTD was shown to specifically interact with P-CTD and a critical interaction site was restricted to the 9 last amino acids of P. To study this interaction, the inventors used for crystallization C-terminal peptides of P restricted to the last 13 residues (P13) down to dipeptide (P2) and the single phenylalanine (P1) in complex with N-NTD. The inventors obtained crystals with P7, P3, P2 and P1. P2 and P1 crystals diffracted to 2.2 and 1.9 Å resolution in a new tetragonal space group with four molecules in the asymmetric unit and in the orthorhombic Nat1 space group, respectively. The Asp-Phe dipeptide or the single Phenylalanine residues were clearly visible in electron density maps. P7 and P3 crystals diffracted to 2.8 and 3.2 Å respectively in orthorhombic Nat2 space group, but further localization of P residues besides the two last C-terminal ones was not possible: the rest of the amino acid chain did not seem to fold upon interaction in the experimental conditions. In all cases, binding did not involve any other structural rearrangements than those already observed within the unbounded crystal forms and the RNP model.

Critical P C-terminal Phenylalanine amino acid was deeply buried in a hydrophobic pocket of N-NTD located between αI2, αN1 and the H151 loop. The P: F241 made a π-π stacking interaction on one side with H151 imidazole ring, which stands on the H151 loop, itself firmly locked by a salt bridge between R150 and D152. On the other face, the benzyl group stacks against the aliphatic and hydrophobic part of R132 side chain, standing on the αI2 helix, and itself in salt-bridge interaction with E128 on the previous turn of the helix. This double stacking is such that the normal axis to the P: F241 benzyl plane will run through NE2 of H151 and CG of R132 firmly interlocking secondary structure elements in N-NTD domain. Perpendicularly to the plane of the benzyl group, a third side of the hydrophobic pocket was closed by Y135, on a third turn of αI2 helix, and remained open on the last side. The bottom of the pocket is constituted by S131, also inserted in αI2 helix turns, M50 and 153 on αN1. In the P2 complex, the negative charge of the C-terminal carboxylate end of Phe was stabilized by K46, H151 and R150. This network of salt bridges and H-bonds stabilized also the charged side chain of the penultimate P: D240 and the carbonyl of this last peptide bond through interactions with R150 and Y135. Finally, a sulfate molecule from the crystallization solution made a bridge between the positive charges of the N terminal end of the peptide, the amide of the last peptide bond and R132 side chain. The phenylalanine benzyl ring was perfectly superimposable in all complexes with P C-terminal peptides. Some electrostatic interactions rearrangements were observed between the Phenylalanine and the Asp-Phe dipeptide complexes, in the other tip of the molecules, more exposed to the solvant, probably essentially reflecting differences in the positioning of their charges and/or in the flexibility of the two molecules. Whatever the two oxygen atoms of the C-term carboxylate of P1 superpose almost exactly on two oxygen atoms of P2, corresponding to its carboxylate end and the carbonyl oxygen of the last peptide link respectively, and the N-terminal amide group of P1 superpose to a solvent exposed oxygen atom in P2, interacting in both cases with the sulfate ion.

Drug Design and Screening

The binding site of Phe on N was used as a target for rational design of potential inhibitors of the N-P interactions. Indeed, this well-defined site has a crucial role for P binding and is composed of residues with high sequence conservation. Based on the structures of the previous complexes with phenylalanine, and the presence in the crystal of a sulfate molecule, we screened the ZINC database for compounds that share with Phe an aromatic ring to be buried in the hydrophobic pocket with further stabilization by electrostatic interactions with R150 [as the C-terminal carboxylate of P-F241] and R132 [as the bridging sulfate molecule]. The screening by AUTODOCK generated a set of approximately 1500 ranked compounds. The set was reduced to approximately 300 compounds by restricting the molecular weight to be lower than 350 g/mol.

Compounds of this set were ordered based on the interaction energy between the ligand and the protein N and the best 50 compounds were selected for further experimental studies.

Backbone Resonance Assignment of N-NTD

The inventors used $^1H$, $^{15}N$ Heteronuclear Single Quantum Correlation (HSQC) NMR spectra to probe the binding of BPdC ligands in solution. To analyze amide chemical shifts we achieved nearly complete sequential backbone assignment of N-NTD from triple resonance experiments: 91% non proline amide $^{15}N/^1H$, 91% $^{13}C'$, 96% $^{13}C\alpha$ and 94% $^{13}C\beta$. For this purpose the protein was 70% deuterated to prevent fast nuclear relaxation mechanisms in this 26 kDa protein. However due to inefficient back-protonation of the amide backbone in $^{15}N^{13}C^2H$ labeled N-NTD, the inventors could not retrieve assignments for the innermost αN3 helix (residues 160-V167). The backbone chemical shifts were analyzed with the Random Coil Index software (Berjanskii and Wishart 2005): the predicted secondary structures are compatible with the topology of the X-ray crystal structures of N-NTD. This provides both a verification of the assignment and a control to compare data between N-NTD in solution and in the crystal.

Determination of the BPdC Binding Site by NMR

Binding of BPdCs to N-NTD resulted in chemical shift perturbations (CSP) in the $^1H$, $^{15}N$ HSQC spectrum of N-NTD. The CSP patterns over the amino acid sequence are similar, which points at similar binding properties. CSPs measured at the titration midpoint were mapped onto the X-ray structure of N-NTD for each ligand. The perturbed residues delineate a region that matches the P-CTD binding site. The largest CSPs, likely induced by an aromatic moiety, are observed in the hydrophobic pocket of N-NTD, at the center of helix αl2 and in the H151-loop, indicating that the BPdCs target the binding site of P-F241. Smaller but yet significant perturbations are observed in the C-terminus of helix αN1 and the two downstream residues (M50-T54), which are also part of this pocket. Moreover two proximal regions are affected: the αl2-η1 loop and both strands of the β-hairpin where it is stacked on αl2.

These regions may be part of an extended contact surface scanned by the BPdCs at the exit of the pocket, but also be subject to conformational rearrangements accompanying ligand binding, since CSPs are sensitive to even minor changes in local geometry. The latter hypothesis is supported by larger variations of $^{15}N$ vs $^1H$ chemical shifts, in particular in the β-hairpin. It would be consistent with the structural variability observed in this region in the different crystal forms of N-NTD as well as with amide chemical shift variations in apo N-NTD induced by small changes in pH and salt concentration.

Affinity Measurements for BPdCs by NMR

The linear evolution of chemical shifts at different ligand: protein ratio indicates a fast chemical exchange regime between free and bound N-NTD, for all five molecules. The population-weighted average chemical shifts were analyzed with a two-site exchange model and a 1:1 stoichiometry, and dissociation constants were extracted for residues with large CSPs.

Kds range between 20 μM for M76 and 680 μM for M72 (M72<M61<M68<M81<M76). Overall the BPdC:N-NTD complexes are weak, but substitutions on the benzyl ring enable modulation of the affinity by a factor of nearly two logs.

Competition Studies by SPR

SPR signals are proportional to the molecular weight of the analytes and therefore, given the small molecular weight of selected compounds, direct binding between N-NTD and BPdC would have too small signals on the used instrument. Instead, the inventors resorted to indirect competition assays to assess the effect of BPdC on the interaction between surface-bound P-CTD and N-NTD. The inventors first characterized by SPR the specific interactions between P-CTD in fusion with GST (GST-P-CTD) and N-NTD. GST-P-CTD was immobilized on an anti-GST antibody surface and serial dilutions of N-NTD were injected. The interaction between the two domains was transient, with a very fast dissociation rate (koff>1 $s^{-1}$) and a Kd of 30 μM. Competition experiments were then performed with the BPdC compounds. M76 and M81 best inhibited the P-CTD/N-NTD interaction with a Ki of 155±25 and 247±39) μM respectively. Both compounds carried a specific Cl substituent in ortho on the benzyl ring, but addition of another Cl atom in para position, on M76, somewhat enhanced inhibition. Other compounds lacking a substitution in ortho position but with alternative F (M72) or Br (M68) substitution in para, or the unsubstituted BPdC appeared to be less potent with Ki of 893±86, 1660±290 and 610±82 μM (M61, M72 and M68), respectively. The inhibitory properties of the compounds were directly related to their affinities for N-NTD with M72<M61<M68<M81<M76.

Biochemical Characterization by ITC

In parallel, the inventors investigated the properties of binding abilities of the di-substituted M76- and unsubstituted M61 to N-NTD by ITC. The purified N-NTD domain was loaded into the calorimeter cell and titrated with the compounds. The data were fitted with a standard model allowing for a set of independent and equivalent binding sites and revealed a stoichiometry of 0.99 consistent with the single binding site observed by Crystallography and NMR. It confirmed the importance of the Cl substitutions of the benzyl with a Kd of 48±8 μM for M76 but 510±170 μM only for M61 with an unsubstituted benzyl ring. Thermodynamic parameters analysis of the ITC isotherms showed that both the binding of M76 and M61 to N-NTD presented were driven by a favorable enthalpic terms: ΔH=−11.0±3.6 kcal·mol-1 for M76 and −6.42±2.42 kcal·mol-1 for M61 which could be associated with favorable electrostatic and van der Waals interactions, partly compensated by unfavorable entropic contributions (−TΔS=5.4±3.8 kcal·mol-1 for M76 and 2.2±1.8 kcal·mol-1 for M61), that may reflect a high flexibility of the compounds leading to this an entropic penalty.

Structures of the N-NTD/BPdC Inhibitor Complexes

The inventors attempted crystallizing N-NTD with all available members of the BPdC family. They obtained three complexes with M76, M81, and M72 at 2.0, 2.7 and 2.9 Å respectively, in the orthorhombic Nat2 space group. They corresponded to the two best and the worst inhibitor, respectively. As for the previous complexes, binding did not induce any structural rearrangement of the globular N-NTD domain. N-NTD residues involved in the binding of the BPdCs were exactly the same as those involved in the binding of the P terminal dipeptide. The substituted benzyl group of the BPdC made the same double staking interactions between R132 on αI2 helix and H151 in the H151 loop as observed for P:F241. As a consequence of the steric (hindrance) occupancy of the halogen substituent(s) on the benzyl cycle, its position slightly adapted in the pocket so that the halogen atom superimposed exactly to the most deeply buried C atom of the benzyl cycle of P1 or P2 complexes. In this conserved double stacking, the H151 imidazole cycle and the m76 benzyl cycle still made a π-π stacking interaction, while on the other side it packed against the planar group of the guanidinium R132 side chain in a well described highly favorable interaction. The normal axis to the M76 benzyl plane ran through NE2 of H151 and NE of R132 located at 3.3 and 4.2 Å, respectively from the benzyl cycle centroid. In addition, the ortho halogen Cl substituent of the benzyl cycle of M76 and M81, deeply buried in the pocket, established a halogen-bond at the bottom of the binding pocket with S131 carbonyl. This interaction is completed by two classical H-bonds between the same ortho-Cl substituent and the hydroxyl of the S131 side chain and the main chain amide of R132, further enhancing charge complementarity. Finally, the second Cl para substituent in M76 made a second halogen bond interacting with a water molecule ideally placed (with a C—Cl-Wat angle close to 170 deg), but also with E128 side chain carboxylate and a second water molecule although the geometry of the bond with the two later atoms is less favorable with C—Cl-Donor angle close to 130-140 deg. The 3 atoms in halogen bond interaction with the Cl-para substituent established altogether a complex network of H-bonds ultimately linked to E112 main chain on the β-hairpin.

The inventors observed synergetic effects between the two Cl substituents of M76 via the benzyl scaffold. This is clearly observed in the final electron density map contoured at high level showing a strong peak around the Cl-ortho substituent while conversely a positive residual density is observed at 3σ in the fo–fc difference map on the Cl-para substituent. Therefore, electrostatic potentials are not identical around the two Cl substituents of M76 when bound to N-NTD. The deformation observed here favors formation of complementary strong H-bonds through the Cl-ortho substituent at the bottom of the binding pocket in addition to the halogen bond established in all cases with the carbonyl oxygen of S131.

Similar halogen-bonding interaction was observed with the F atom in para on the benzyl cycle in the non-inhibitory compound M72 and consequently induced a radically different orientation of the benzyl ring in the pocket. As a consequence of the radically different orientations of the benzyl group in the binding pocket, the pyrazole cycles of M76, M81 and M72 differed in their interactions with the binding pocket of N-NTD. In the two first complexes, the BPdC pyrazole cycle made another π-π stacking interaction with Y135. In this case, the orientation of the pyrazole cycle is also favored by direct salt-bridge interactions of its two carboxylate groups with R132 and R150 located on both sides of the pocket, on αI2 helix and H151 loop respectively. This stacking interaction between the BPdC pyrazole cycle and Y135 did not occur with M72, resulting in a loss of interactions and a pyrazole cycle orientated roughly at 90 deg., as compared to the pyrazole cycle of M76 or M8. In this orientation, the two carboxylate substituents of M72 interacted solely with R150. Finally, while a very good complementarity in charge and shape was observed for M76 and M81 binding in the binding pocket of N-NTD, it was not the case with M72, easily explaining their relative affinities and inhibitory properties.

CONCLUSION

1) N-NTD: P-CTD Complexes Provide Models of the RNA-N:P Interaction

By site-directed mutagenesis and using a polymerase activity assay, based on an HRSV minigenome containing a luciferase reporter gene, the inventors have previously identified the P-binding region on RNA-N complexes as a pocket located on the N-terminal domain of N. They also obtained the atomic structure of the N protein in a nucleocapsid-like complex with RNA by crystallizing RNA-N rings containing 10 protomers of recombinant N.

To further characterize the binding properties of the pocket of N containing critical residues for in vitro transcription/replication, the inventors designed a simpler system than RNA-N rings. The N-NTD construct (N[31-252]), produced in a monomeric RNA-free form provided the starting point for modeling the N: P interactions. The X-ray crystallography structures of N-NTD reported here confirmed that N-NTD reflects the structural properties of the N-terminal domain in authentic RNP.

The inventors first addressed the structure of the RSV RNP: P complexes. The N-NTD was used to probe short peptides from the C-terminal domain of P previously identified as binding to the RNA-N domain. The crystal structures obtained here with P1 (phenylalanine), P2 (Asp-Phe dipeptide), P3 and P7 show that these peptides inserted into the aforementioned pocket, supporting the idea that the reduced N-NTD: P-CTD complexes were indeed models for the RNP: P interaction. Binding of the peptide ligands did not significantly disturbed the organization of the pocket as deduced from the comparison between apo and P1 or P2-bound structures. Only the last P:F241 or the two last residues seemed required for binding of P, since no electron density was found for the upstream residues in P3 and P7.

These structures highlighted a number of determinants driving the N-NTD and P-CTD interactions:
(i) the aromatic moiety of P1 and P2 was stabilized by aromatic π-π stacking interaction with the imidazole ring of H151 in the H151 loop;
(ii) the other phenyl face of P: F241 was anchored to the αI2 helix by hydrophobic interactions with R132,
(iii) R132 was engaged in a salt bridge with E128, and with S131 and Y135 defining the bottom and an edge of the pocket respectively, all located within three turns of the αI2 helix, in an organization also present in the apo form.

These interactions seemed constituting the driving force for all P peptides complexes. The exposed and highly polar remaining part of the P2 peptide, particularly the negatively charged C-terminal carboxylate, the P: D240 side chain carboxylate and the carbonyl of the last peptide bond, are counteracted by the positive patch of K46, R150, H151 and Y135. Taken together, a picture emerged of a highly structured target pocket that is essentially filled by P: F241 aromatic side chain. The key role of P: F241 in P peptides binding was in line with the total loss of RNA polymerase activity and binding to RNA-N by F241 deletion from P. In all structures, the target pocket was readily accessible as reflected by the fast dissociation of the ligands observed in NMR and SPR experiments.

2) The P-Binding Site on N-NTD is a Druggable Pocket

The detailed molecular view of the N-NTD with P-CTD interaction was essential for the docking of potential antivirals that could interfere with P binding to N. The main determinants targeted by simulations were
  (i) stacking interactions of an aromatic ring of the ligand with H151 and R132 as observed with P: F241;
  (ii) electrostatic interactions with R150 and R132, mimicking P: F241 interactions and replacing the sulfate ion. Screening of compounds for binding to the P-binding pocket of N-NTD was carried out in silico and resulted in 50 molecules. The BPdC molecules shared a scaffold that mimics the phenyl ring of P1 and P2, and two carboxylates reminiscent of the carboxylates present on P1 and P2 as well as of the co-crystallized sulfate.

Binding of BPdC ligands involved a double stacking interaction with H151 and R132 as observed with P1, P2 bound. Both imidazole H151 stacking on the benzyl ring of the ligand and the guanidinium of R132 interaction with the benzyl ring of the ligand pair adopted the most energetically favorable arrangement, namely, NE2 and NE atoms of H151 and R132 located on both sides of the benzyl cycle centroid at 3.3 and 4.2 Å respectively. These optimal interactions were further stabilized by a complex electrostatic network including halogen bonds and hydrogen bonds formations at the bottom of the pocket.

Distinct features of the BPdC ligands were their ability to bridge between αI2 helix and H151 loop, allowing rigidifying the cavity. While the primary driving force was the double stacking interaction, only a relatively weak interaction was sufficient to induce the conformational change of the ligand seen in the crystal structures by rotation of its benzyl ring in the cavity. This fine-tuning had long-range consequences on ligand binding since it determined the orientation of the second half of the molecule, namely the pyrazole di carboxylate moiety. Indeed, a very nice complementary interaction is observed in this second part of the molecule with a new π-π stacking interaction between the pyrazole cycle and Y135 for ortho substituted M76 and M81 ligands and the two carboxylate substituents of this second aromatic cycle made direct salt bridges with R150 and R132 further tightening the interaction with αI2 helix and H151 loop.

However, CSP patterns over the amino acid sequence were globally similar for all BPdCs, showing that the five ligands shared similar binding properties and suggesting that in solution the dicarboxylate moiety could be rapidly exchanging between different orientations at the exit of the binding pocket, two of them being trapped in the crystal structures with M72 and M76. NMR also suggests that two mobile regions of N-NTD are involved in BPdC binding: the αI2-α1 loop (residues G143, E144) and the β-hairpin, which are both slightly displaced in the different crystal forms. They display large $^{15}$N CSPs and ligands with comparable substitutions on the phenyl moiety, i.e. M68 and M72 both with a single para halogen substitution, or M76 and M81 both with an ortho chlorine, yield similar CSP sub-patterns. These results can be interpreted as small changes of backbone geometry that compensate for BPdC fitting in the pocket. Rearrangements within the β-hairpin are transmitted through inter-strand hydrogen bonds or by bound water molecules like in M76, as observed in the X-ray structure.

The crystal structures of N-NTD in complex with BPdC ligands revealed two other sources of stabilization for M76, i.e. formation of a halogen bond between M76 and S131 with synergetic effects from the second halogen and solvent contribution to the binding. The fine tuning of the optimal position of the benzyl ring was partly driven by halogen-protein interactions. S131 was the best candidate for tuning this halogen-protein interaction. The role of Ser131 in positioning the ortho Cl of M81 and M76 is reminiscent of specific interaction of halogen bond donors that can be made with halogenated ligands, depending on their availability in the binding site of proteins. The nucleophile atoms of amino acid main- and side-chains were shown to be halogen bond donor (Lewis base) under specific geometric (distance and angles) requirements.

A tighter interaction by roughly half an order of magnitude was found by addition of a Cl substituent in ortho position in M81 compared with M61. The best BPdC inhibitor was the di-Cl substituted M76. Although Fluorine is capable of forming halogen bonds, albeit weakly, the F para substituent in M72 established a noteworthy similar interaction with S131 at the bottom of the binding pocket.

Interestingly, Br was clearly favored compared to the F substituent, an affinity order predicted from the effect of electronegativity of halogen substituent in halogen bonds: stronger halogen bonds are made with larger halogen atoms. Moreover, the comparison of M72 and M61 affinities suggests that an unfavorable substituent as fluorine even decreased the interaction.

In M76, S131 was found in close proximity with the ortho Cl and only the carbonyl oxygen atom of S131 was at a distance (3.9 Å) and angle (150 deg.) requested for such an interaction. The remaining polar contacts at less than <4 Å around this Cl atom are such that S131 side chain hydroxyl (OG) and R132 main chain NH groups donate hydrogen bond directly toward the negative belt of the Cl substituent in a side-on contacts with electrophile atoms.

The second para Cl substituent in M76 formed a strong halogen bond with a primary water molecule located at nearly ideal≈175 deg. C.—Cl—O angle, but also with E228-OE2 (132 deg.) and a secondary water molecule (140 deg.). All three atoms are themselves in H-bond interactions leading to E112 on the nearby β-hairpin. Strong interactions in this region were also revealed by NMR amide CSPs, for E112 and R101. Synergic effects of the ortho and para Cl substituents on M76 binding were observed. Introducing an additional Cl substituent affected the σ hole, involved in head-on halogen bond formation, the negatively charged belt lateral to the C—Cl bond, involved in side-on H-bond formation, and the negatively charged π cloud of the benzyl scaffold. Indeed, the final 2fo–fc electron density map showed a strong peak at 2σ around the Cl-ortho substituent and still some density around the lighter C/O/N atoms of the ligand while there was no remaining density around the Cl-para substituent. Conversely a positive residual density is observed at 3σ in the fo–fc difference map on the Cl-para substituent. These data supported the hypothesis of a synergy that strengthened the halogen bond with Cl-para and the H-bonds with Cl-ortho at the bottom of the binding pocket.

Water molecules thus stabilized M76 binding. In addition to the water molecule involved in halogen bonds, both carboxylates substituting the pyrazole cycle established new contact with N-NTD via bridging water molecules to Y135-OH, R132-O, R150-NH2 and E144 carboxylate. The later residue is located on the αI2-η1 loop and NMR shows here again an effect on its amide CSP, notably with M76 and M81. This network of interactions mediated by water molecule is likely to further stabilize the pyrazole cycle stacking with Y135. Furthermore it explains how this rather small molecule can induce measurable effects from the outer side of the β-hairpin up to the αI2-η1 loop at the other side of the N-NTD domain. A detailed examination of the binding pocket also showed the nearby presence of an internal cavity in N-NTD, large enough to accommodate several water molecules, and flanked by conserved residues.

In all ligand-bound complexes, this highly organized water network was linked to the ligand binding site via E112, E128 and sometimes R132 and may contribute to ligand stabilization. The cavity and water molecule were also observed in the absence of ligand. The presence of conserved and organized water molecules toward the bottom of the cavity suggested that the cavity might accommodate a more extended ligand.

3) Comparison with Other RNP:P Complexes/Specificity of N-NTD:P-CTD Interaction in Pneumovirinae The structure of the RNP:P complex in RSV cannot be simply translated to structural data available for other Mononegavirales, including the nucleoprotein. The nucleoproteins display structural homology with a highly conserved fold and similar RNA binding groove and flexible arms that lock lateral N-N interactions in the RNP. However, the structure of the C-terminus of the P proteins differs. RSV seems to have developed yet an alternative strategy for the RNP:P interaction, where only the very last two C-terminal amino acids insert into a binding pocket with a predefined fold. The P binding site is located on the ridge formed by the bulky N-NTD domain projecting away in the RNP helix, and this region of N was rated as the most divergent in the three-dimensional structures of N of Mononegavirales. Indeed this is an advantage for drug development and M76 can thus be described as a "lead" molecule with comparable micromolar affinity. By extension of the molecule by fragment-based design, optimization of its affinity for N-NTD is possible based on solid structural grounds provided by this study. Any efficient drug targeting this site will be highly specific for Pneumovirinae.

Example 2

Compounds According to the Invention Inhibiting the Replication of a Recombinant RSV Virus in Cell Cultures The inventors have further developed a new compound, which proved to show promising effects in therapy, as follows;

(M76b)

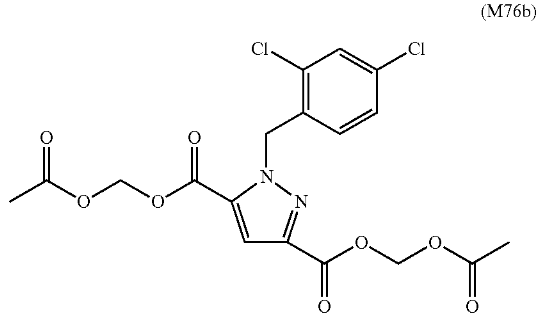

1) Process of Preparation

The pH sensitive prodrug M76b, 1-(2,4-Dichloro-benzyl)-1H-pyrazole-3,5-dicarboxylic acid diacetoxymethyl ester, was designed by fixing acylal group on both carboxylic acids of the pyrazole diacid. The product has been prepared by alkylation of the diisopropylethylammoniun salts of 1-(2,4-dichloro-benzyl)-1H-pyrazole-3,5-dicarboxylic acid by bromomethyl acetate in a polar solvent. The crude product could be purified by flash chromatography over silica gel.

1-(2,4-Dichloro-benzyl)-1H-pyrazole-3,5-dicarboxylic acid diacetoxymethyl ester To a solution of 1-(2,4-dichloro-benzyl)-1H-pyrazole-3,5-dicarboxylic acid (90 mg, 0.28 mmol) in DMF (2 mL) was sequentially added i-$Pr_2$NEt (0.5 mL, 2.8 mmol) and bromomethyl acetate (171 mg, 110 μL, 1.12 mmol). The reaction mixture was stirred at room temperature for 16 h and concentrated under reduced pressure. The oily residue was taken up into ethyl acetate (20 mL) and washed with aqueous sodium bicarbonate (2 mL) and brine (2 mL). The organic phase was dried over $MgSO_4$ and concentrated under reduced pressure to leave a yellow which was purified by chromatography over silica gel eluting with AcOEt/cyclohexane, 2:1 to give the title compound as a colorless oil (102 mg, 78%). IR (neat) ν: 3146, 3000, 1769, 1765, 1736, 1591, 1565, 1530, 1476, 1443, 1368, 1259, 1230, 1213, 1187, 1171, 1156, 1087, 1048, 1024, 1101, 985, 956, 861, 836, 811, 760, 739, 685 $cm^{-1}$, $^1$H NMR ($C_6D_6$, 300 MHz) δ: 7.46 (s, 1H), 7.01 (d, J=2.1 Hz, 1H), 6.62 (dd, J=8.4 Hz, J=2.1 Hz, 1H), 6.28 (d, J=8.4 Hz, 1H), 5.77 (s, 2H), 5.50 (s, 2H), 5.48 (s, 2H), 1.48 (s, 6H), $^{13}$C NMR ($C_6D_6$, 300 MHz) δ: 168.9 (CO), 168.6 (CO), 159.8 (CO), 157.3 (CO), 142 (C), 134.4 (C), 133.6 (C), 133.2 (C), 132.8 (C), 129.6 (CH), 129.0 (CH), 127.5 (CH), 115.8 (CH), 79.5 ($CH_2$), 79.4 ($CH_2$), 53.3 ($CH_2$), 20.0 ($CH_3$), 19.9 ($CH_3$).

2) Monitoring of rHRSV-m Cherry Replication in Cell Culture

The inhibition of RSV replication by M76b was measured in cell cultures using an assay based on a recombinant human RSV reverse genetics system in which the red fluorescent protein mCherry was inserted into the RSV genome, rHRSV-mCherry described in (Rameix-Welti et al., Nature Communications, 5:5104 (2014)).

Compound M76b was solubilized at 10 mM in 100% v/v DMSO and further diluted in water to 1 mM, then serially diluted threefold in minimum essential medium (MEM) without phenol red (Gibco) to a final concentration of 5 nM. DMSO dilutions in the same range were also used as controls. HEp-2 cells (ATCC number CCL-23) were seeded at $5\times10^4$ cells per well in 96-well plates the day before. Infection was carried out with 500 pfu of rHRSV-mCherry in MEM without phenol red. 2 h after infection, the medium was changed to MEM with 2% fetal calf serum and without phenol red. Compound dilutions were pre-incubated with viral suspensions for 5 min at 37° C. before addition on cell monolayers in the 96-well plates. After treatment with compound M76b in DMSO or with DMSO alone, plates were incubated at 37° C. and 5% $CO_2$ for 48 h.

Fluorescence, expressed in relative fluorescence units, was measured using a spectrofluorimeter (Tecan infinite M200PRO) with excitation and emission wavelengths of 580 and 620 nm, respectively. Non-infected HEp-2 cells were used a standard for fluorescence background level. The fluorescence of infected HEp-2 cells was normalized with the mean control value obtained from 12 wells with infected cells without M76b or DMSO.

Cytotoxicity was assayed with the CellTiter-Glo Luminescent cell viability assay (Promega) after 48 h of incubation with DMSO alone or threefold dilutions of compound M76 in DMSO from 1 mM to 12 μM.

3) Compound M76b Displays Inhibitory Activity for Recombinant RSV Replication

Expression of the red fluorescent mCherry protein in cell culture is correlated with the infection rate of rHRSV-mCherry and allows monitoring of RSV multiplication. Under the experimental conditions described above, fluorescence was clearly decreased by M76b in a dose dependent manner, with less than 20% relative fluorescence at 333 µM M76b, as compared to the control done in the absence of M76b and DMSO. At 111 µM M76b, the relative fluorescence was 40%. Fluorescence values in the same range as the untreated controls, i.e. above 80%, were measured for M76b concentrations under 12 µM. Control experiments were done with DMSO alone and showed that the relative fluorescence was not affected by the addition of DMSO, with relative intensities varying between 80 and 120% in a random fashion. Finally biases arising from possible cytotoxicity of DMSO and M76b were evaluated, using the same incubation time as for viral replication. The amount of DMSO equivalent to that added with 1 mM M76b induced 40% cell death, but a threefold dilution (I.e. with an amount of DMSO equivalent to that added with 333 µM M76b) already reduced cell death due to DMSO to less than 5%. At 333 µM, M76b showed a cytotoxic effect with only 25% cell survival, but at 111 µM M76b, cell survival was more than 95%. Taken together these results show that M76b is able to inhibit recombinant RSV replication without inducing cytotoxicity, with a small but still promising therapeutic window between 10 and 100 µM.

In light of the crystal structures previously obtained with the doubly hydrolyzed form of M76b, it was hypothesized that negatively charged groups on the pyrazole ring should participate in driving the binding of compounds with a 1-Benzyl-1H-Pyrazole-3,5-diCarboxylates scaffold to RSV nucleoprotein in the context of the RSV nucleocapsid. However charges greatly hinder crossing of plasma membranes. Thus, the inhibitory activity on RSV replication observed with electrically neutral M76b, in which the two carboxylates were protected of by esterification, suggests that M76b was successfully internalized by the cells and that the ester bonds were subsequently hydrolyzed for binding to the previously identified hydrophobic cavity on RSV nucleoprotein.

The invention claimed is:

1. A method for treating an infection by respiratory syncytial virus (RSV), comprising administering to a subject an agent, wherein said agent is represented in formula (I):

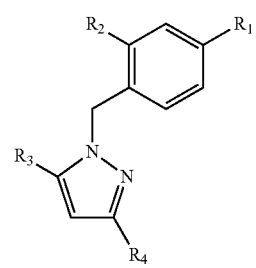

Formula (I)

wherein:
R1 and R2 are identical or different and are independently chosen among hydrogen, hydroxyl, halogen, haloalkyl, alkyl, aryl, arylalkyl, nitro, cyano, amino, alkoxy, alkoxyalkyl, heteroaryl, cycloalkyl and heterocyclyl; and R3 and R4 are identical or different and are independently chosen among carboxylate, ester, substituted or non-substituted alkyloxycarbonyl, halogen, haloalkyl, alkyl, aryl, arylalkyl, nitro, cyano, amino, alkoxy, alkoxyalkyl, heteroaryl, cycloalkyl, heterocyclyl, boronate, phosphate, phosphonate, sulfinyl, sulfonyl, sulfonate, and sulfonamino, sulfonamido.

2. The method according to claim 1, wherein R3 and R4 are identical and are both carboxylate.

3. The method according to claim 1, wherein R1 and R2 are identical or different and are independently a halogen independently selected from the group consisting of: fluorine (F), chlorine (Cl), bromine (Br), and iodine (I).

4. The method according to claim 1, wherein R1 and R2 are identical and are both hydrogen.

5. The method according to claim 1, wherein R1 is fluorine and R2 is hydrogen.

6. The method according to claim 1, wherein R1 is bromine and R2 is hydrogen.

7. The method according to claim 1, wherein R1 is hydrogen and R2 is chlorine.

8. The method according to claim 1, wherein R1 and R2 are identical and are both chlorine.

9. The method according to claim 1, further comprising administering an antiviral agent with the agent of formula (I) as a combined preparation for simultaneous, separate or sequential, wherein said antiviral agent is selected from the group consisting of acyclovir, cidofovir, docosanol, famciclovir, foscarnet, fomivirsen, ganciclovir, idoxuridine, penciclovir, peramivir, trifluridine, valacyclovir, vidarabine, lamivudine, and ribavirin.

* * * * *